United States Patent
Mitra et al.

(10) Patent No.: US 6,617,847 B2
(45) Date of Patent: Sep. 9, 2003

(54) SENSING DEVICE FOR THE NON-DESTRUCTIVE EVALUATION OF STEEL STRUCTURES OR COMPONENTS

(75) Inventors: Amitava Mitra, Jamshedpur (IN); Sarmistha Palit Sagar, Jamshedpur (IN); Dipak Kumar Bhattacharya, Jamshedpur (IN)

(73) Assignees: Department of Science & Technology, New Delhi (IN); Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/045,033

(22) Filed: Apr. 19, 2002

(65) Prior Publication Data

US 2002/0196016 A1 Dec. 26, 2002

(30) Foreign Application Priority Data

Jan. 15, 2001 (IN) ........................................ 29/DEL/2001

(51) Int. Cl.[7] .......................... G01B 7/24; G01N 27/72; G01R 33/12
(52) U.S. Cl. ........................................ 324/209; 324/240
(58) Field of Search ................................ 324/209, 239, 324/240, 241, 242, 243, 236, 237, 238, 262

(56) References Cited

U.S. PATENT DOCUMENTS

| | | |
|---|---|---|
| 5,059,903 A | 10/1991 | Otaka et al. |
| 5,121,058 A | 6/1992 | Allison et al. |
| 5,142,227 A | 8/1992 | Fish |
| 5,166,613 A | 11/1992 | Perry |
| 5,729,135 A | 3/1998 | Kugai |
| 5,854,492 A | 12/1998 | Chinone et al. |

*Primary Examiner*—Walter E. Snow
(74) *Attorney, Agent, or Firm*—Shlesinger, Arkwright & Garvey LLP

(57) ABSTRACT

The present invention relate to a device for the non-destructive evaluation of such structures and components as are in service and which are intended to continue in use for an extended period during which time a number of defects such as residual stress, fatigue, creep or the formation of magnetic phase in non-ferromagnetic steel can develop; in addition to its primary purpose of detecting and/or determining the stated defects in-service steel structures or components, the device of the present invention also possesses the advantage that it can be applied for the sorting and classification of steels of different compositions according to the results of defects detected.

11 Claims, 1 Drawing Sheet

Figure 1:
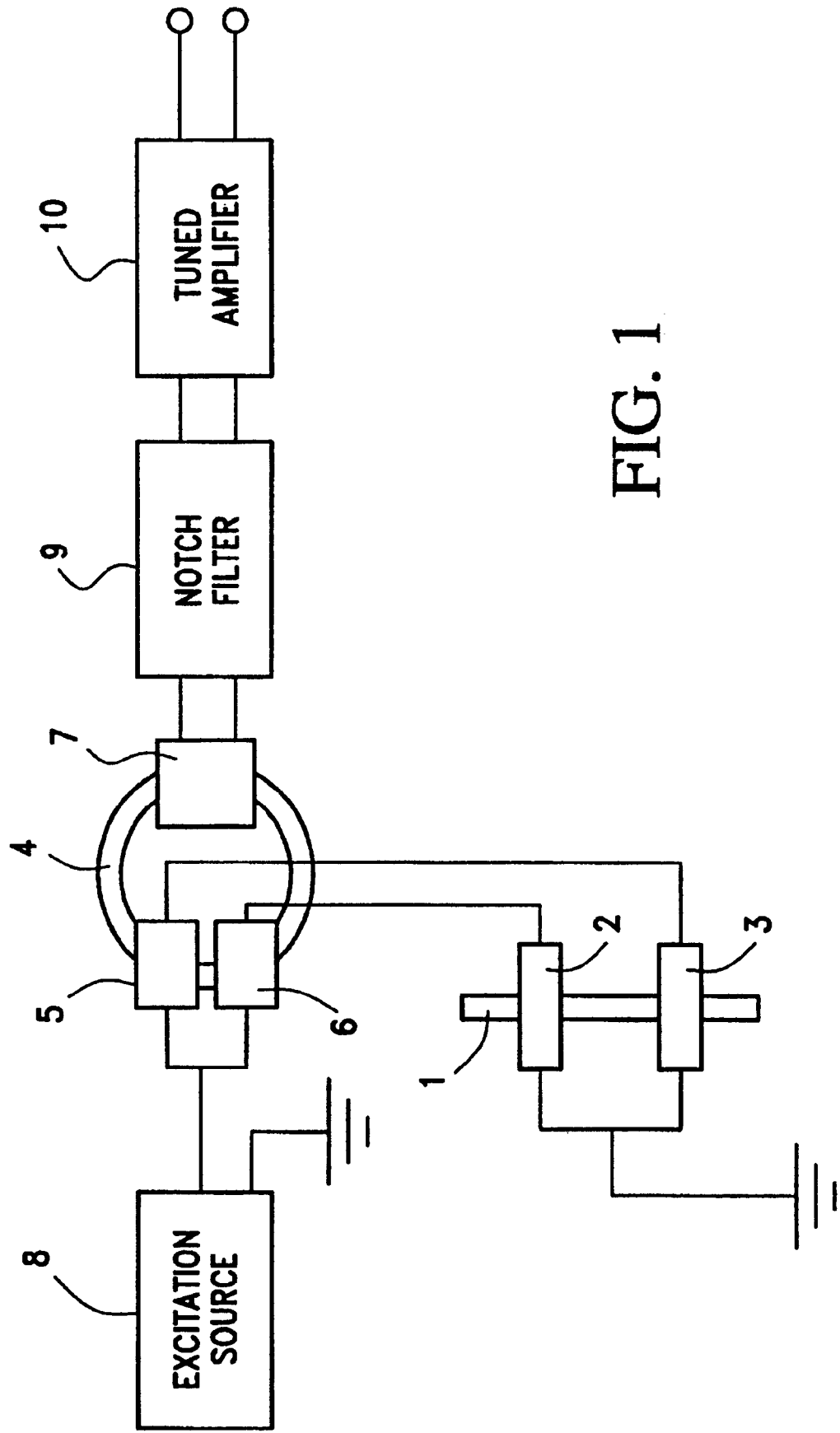

SENSING DEVICE FOR THE NON-DESTRUCTIVE EVALUATION OF STEEL STRUCTURES OR COMPONENTS

FIELD OF THE INVENTION

The present invention relates to a device for the non-destructive evaluation of service-exposed steel structures and/or components. More specifically, the invention relates to a device for the non-destructive evaluation of such structures and components as are in service and which are intended to continue in use for an extended period during which time a number of defects such as residual stress, fatigue, creep or the formation of magnetic phase in non-ferromagnetic steel can develop. Thus, in addition to its primary purpose of detecting and/or determining the stated defects in in-service steel structures or components, the device of the present invention also possesses the advantage that it can be applied for the sorting and classification of steels of different compositions according to the results of defects detected.

The determination of the presence of residual stress in critical areas of in-service components is most desirable since the undetected presence of such stresses can cause failure of such components or structures. Likewise, the determination of micro-structural degradation within in-service steel structures and components is invaluable as an early warning system to guard against sudden failure of those components and structures. Most of all, the presence of magnetic phase above a critical percentage in certain non-magnetic stainless steel structures or components is to be avoided at all costs for the reason that such magnetic phase may cause brittle fracture of the structure or component in question. It is, therefore, accepted that the determination of the presence or absence of such magnetic phase is vital.

BACKGROUND ART

In the past, the determination of the presence of magnetic phase, residual stress or micro-structural degradation in steel structures or components has most often been effected by employing an x-ray diffractometer and/or by metallographic analysis of the steel in question. Another technique for the magnetic non destructive evaluation of ferromagnetic materials is what is known as the Magnetic Barkhausen Emissions (MBE) technique. Unfortunately, all these methods for the determination of the presence of magnetic phase suffer from serious drawbacks.

For instance, to attempt to effect on site experimentation with an X-ray diffractometer is at the best of times not easy and on some occasions quite impossible. Portable X-ray diffractometers currently available for the measurement of residual stress in components are very expensive to purchase. What is more, although described as "portable", these diffractometers are not easily transportable from one site to another and their use can be rendered totally impossible by their inaccessibility to the location of the components to be investigated.

Metallographic analysis for the quantitative estimation of the presence of a low volume percent of ferromagnetic martensite phase is not only difficult but also inaccurate and the presence of such a low percentage cannot be assessed quickly at site.

The third possible non-destructive technique for determination of ferromagnetic phase, namely the MBE technique, suffers from the shortcoming that it is not sensitive when the presence of martensite is less than 20%.

Techniques for the non-destructive evaluation of ferromagnetic materials have been fairly widely described in the prior art. Thus, magnetic techniques for determination of the degradation of components based on the hysteresis properties of the material of such components have been disclosed in U.S. Pat. No. 5,059,903 entitled "Method and apparatus utilizing a magnetic field for detecting degradation of metal materials" and in U.S. Pat. No. 5,142,227 for "Method and apparatus for measuring strain within a ferromagnetic material by sensing change in coercive force". However, magnetic hysteresis technique is not particularly sensitive to the presence of a very low amount of magnetic phase. For example, such technique is not suitable for the determination of less than 20% martensite in work hardened AISI 304 stainless steel. Moreover, it requires a power source to energise the electromagnet employed by the technique.

U.S. Pat. No. 5,166,613 entitled "Method and apparatus for mapping stress within ferromagnetic materials by analysing Barkhausen noise formed by introduction of magnetic fields" and U.S. Pat. No. 5,121,058 entitled "Method and apparatus for useing magneto-acoustic remanence to determine embrittlement" reveal that the embrittlement of steel can be studied by means of the MBE technique or magneto-acoustic emissions technique as referred to therein. However, each of these techniques requires thorough signal analysis and hence the equipment involved is both costly and complicated. Moreover, the sensitivity of the devices disclosed in these two U.S. Patents is low.

On the other hand, extremely sensitive equipment, e. g. the superconducting quantum interference device (SQUID), for determination of small changes in magnetic properties is known and has been described in U.S. Pat. No. 5,729,135 entitled "Non-Destructive Testing Equipment Employing SQUID Type Magnetic Sensor In Magnetic Shield Container" and in U.S. Pat. No. 5,854,492 entitled "Superconducting Quantum Interference Device Fluxmeter And Non-Destructive Inspection Apparatus". However, SQUID is a very expensive device which requires liquid helium or liquid nitrogen as coolant for its operation and is not truly portable for field work.

An overall object of the present invention is to provide a device for the non-destructive evaluation of the presence of magnetic phase in steel structures or components which device overcomes the deficiencies and shortcomings of hitherto known devices for this purpose.

Within such overall framework, it is a basic object of the invention to provide a device for the non-destructive evaluation of the presence of magnetic phase in steel structures or components which in their virgin state are non-magnetic but which acquire a magnetic presence in the course of extended periods in service.

A more specific object of the invention is the provision of a low cost, portable easy to use magnetic sensing device for the non-destructive evaluation of steel structures or components which have undergone an extended period of service in order to determine the extent of micro-structural degradation which has taken place or the residual stress which has been generated in said structures or components during such period of service.

A still further object of the invention is the provision of a device which while capable of the non-destructive evaluation of steel structures or components for the detection of magnetic phase also affords the advantage of use as an apparatus for the sorting and classification of steels of different composition according to the results of defects detected by said device.

Yet another object of the present invention is to provide a device which for reason of its ability to detect even very weak magnetic fields can be employed as part of a security system for detecting the movement of ferromagnetic objects taking place at varying distances.

Towards achieving the objects stated, the present invention has particularly investigated and researched the aspect of the sensor mechanism employed by prior art devices for the non-destructive evaluation of the presence of magnetic phase in ferromagnetic materials. This has led to the conclusion that an improved construction comprising a sensing core and a toroidal core with respective sets of coils optimally located with respect to such cores and the use of a predetermined material for the sensing core could overcome substantially the drawback described and provide the solution to the problems which the invention seeks to resolve.

SUMMARY OF THE INVENTION

Accordingly, the present invention provides a portable, easily operable magnetic sensing device for the non-destructive evaluation of steel structures of components which have undergone an extended period of service in order to determine the extent of micro-structural degradation or residual stress within said structures or components which comprises the combination of a probe head adapted to be located proximate the structure or component to be evaluated and signal processing means, characterised in that said probe head comprises a sensing core of nanocrystalline Fe-based material having a first pair of coils wound thereabout such that in normal condition when current flows through said first pair of coils, each half of the sensing core is symmetrically magnetised and said processing means comprises a toroidal ferrite core having a second pair of coils wound thereon, one of the terminals of each of said first pair of coils of the sensing core being earthed while the other terminals thereof are each connected respectively to one terminal of each of said second pair of coils on said toroidal core, the other terminals of the second pair of coils being joined together and connected to an excitation source capable of generation of a frequency of 5 kHz, the combination of said first and second pairs of coils constituting a primary coil, the sensed signal having different harmonics which emanates from said primary coil when the probe head is placed proximate a structure or component being evaluated in order to assess the micro-structural degradation or residual stress thereof being transmitted to the input of a secondary coil mounted on said toroidal core, the output of said secondary coil being connected to a filter means active to suppress only a first harmonic signal and to permit other harmonic signals to pass onward for measurement thereof.

DETAILED DESCRIPTION OF THE INVENTION

According to a preferred feature of the invention, the nanocrystalline Fe-based material forming said sensing core is a heat-treated $Fe_{72+x}Nb_{4.5-x}Cu_1Si_{13.5}B_g$ in which x is a value from 0 to 1, said nanocrystalline ribbon having the following approximate properties:

Dimension: 40 mm×10 mm×24 f.im

Permeability: $10^4$–$10^5$

Coercivity: 10–30 mOe

Saturation induction: 8–10 kG

Conveniently, the toroidal core is composed of a Mn-Zn ferrite having a permeability of from 3000 to 4000 and coercivity of from 1 to 3 Oe.

A preferred filter means for use with the device of the invention is a notch filer which acts to suppress the first harmonic, i.e. a signal of 5 kHz, and to permit other harmonics, i.e. all signals other than those of 5 kHz, to pass onward.

The amplitude of the second harmonic signal can be measured by any conventional means such as a multimeter. Such signal may be measured direct or might first be amplified by passage through an amplifier connected to the output of said filter means. Preferably, the amplifier employed is a tuned amplifier, which amplifies the second harmonic, i.e. a signal of 10 Hz, to a desired level for the convenient measurement thereof.

The construction of the probe head and the toroidal core, which act in combination as the main sensor unit, constitutes an essential part of the novelty of the device of the invention. The successful achievement of the objects, which the invention has set itself lies in the construction of this sensing unit and resides in the proper positioning of coils on the sensing core as well as on the toroidal core and the use of nanocrystalline ribbon as sensing core.

The device of the present invention will now be described in greater detail with reference to the accompanying drawing in which the single figure shown depicts a schematic view of the invention device.

Referring to the drawing, the device consists of a probe head H composed of a first pair of coils 2 and 3 coupled about a sensing core 1 of nanocrystalline Fe-based material. One terminal of each of coils 2 and 3 is earthed while the opposite terminals thereof are connected respectively to the input terminals of a second pair of coils 6 and 5, the combination of said first (2,3) and second 5,6) pairs of coils constituting a primary coil. The second pair of coils 6 and 5 also forms part of processing means P. This processing means P comprises a Mn-Zn ferrite toroidal core 4 on which said second pair of coils 5 and 6 are mounted and a secondary coil 7 also mounted on said toroidal core 4. The second pair of coils 5 and 6 are connected together through their opposite terminals to an excitation source 8. Secondary coil 7 provided on toroidal core 4 is adapted to pick up the sensed voltage of the component being evaluated.

The coils are so wound that in normal, i.e. non-evaluating, mode, when current generated by excitation source 8, which may conveniently be a constant current signal generator, flows through the coils, each half of sensing core 1 is symmetrically magnetised. In this mode, the signal picked up at the input of secondary coil 7 will not have any even harmonics. On the other hand, when the device is in evaluating mode, that is when probe head H comprising the assembly of sensing core I and primary coils 2 and 3 is placed close to a component or structure to be evaluated for the presence of micro-structural degradation or residual stress, the signal picked up at the input of secondary coil 7 will have even harmonics. Such picked-up signal is then passed from the output of secondary coil 7 through notch filter 9 on to tuned amplifier 10 to obtain an amplified second harmonic signal which is capable of being monitored and measured by any conventional means such as a multimeter. Alternatively, the amplified signal may be interfaced to a computer.

The voltage of excitation source 8 is maintained within the range of 4 to 5 volts and the excitation frequency at about 5 kHz. Notch filter 9 to which the signal picked to up by tertiary coil passes is designed to allow the entire sensed signal to pass other than the first harmonic, that is a signal having a frequency of 5 kHz. Tuned amplifier 10 to which the filtered signal passes is constructed to amplify only the second harmonic, i.e. the portion of the signal having a frequency of 10 kHz.

Each of the first pair of coils 2 and 3 are provided with the same number of turns which vary between 1500 and 2000. The number of turns of each of the second pair of coils 5 and 6 are likewise the same and vary from 25 to 50. The number of turns of secondary coil 7 can vary from 50 to 100.

To illustrate the efficiency of the device of the present invention as a sensor for the non-destructive evaluation of in-service steel structures or components in order to determine the extent of micro-structural degradation or residual stress therein certain tests were carried out. The results of such tests are set out hereafter. However, these are only by way of example and must not therefore be construed to limit the scope of the invention in any way.

TEST 1

Detection of Ferromagnetic Phase in Austinitic Stainless Steel

As is well known, austenitic stainless steel is non-magnetic. On the other hand, martensite, which is the hard constituent of which quenched steel is composed, is ferromagnetic. Hence, stainless steel which contains martensite as a minor phase will behave as a ferromagnetic material with a magnetic strength dependent on the quantum of martensite present. Based on this understanding, an initial experiment was carried out to test the efficacy of the sensor device of the invention.

AISI 304SS steel was plastically deformed by cold rolling to different extents in order to obtain samples containing different percentages of martensite. When the probe head of the device was placed proximate the samples thus obtained, a linear variation of the sensor output voltage was observed up to 25 vol % content of martensite. Above that level of martensite, the linearity of the sensor was disturbed. In the linear region, the slope became 17 m V per vol % of martensite.

The results of this experiment indicate that the sensor device of this invention will be useful for the determination of amounts as low as 6% by volume of martensite in work hardened AISI 304 stainless steel.

TEST 2

Detection of Delta Ferrite Percentage in Austinitic Stainless Steel Samples Four controlled austenitic stainless steel weldment samples with different delta ferrite content were employed in this experiment. The percentage of delta ferrite in each had been estimated earlier by quantitative metallographic method. The ferrite numbers (FN) of the samples were 0.4, 1.8, 2.3 and 3.6. A linear increase of the sensor output voltage with the ferrite number was observed and the results indicate that the sensor can detect down to 0.4 FN in weldments.

TEST 3

Detection of Varying Presence of Carbon in the Composition of Steel

It is well known that the properties of steel and the various phases it exhibits vary with the carbon content thereof. With this in mind, this experiment was carried out to attempt to find the response of the sensor device of this invention to steel containing a varying degree of carbon percentages. Five grades of steel were considered containing 0.24%, 0.048%, 0.08%, 0.14% and 0.15% by weight of carbon, the other alloying elements of the steel being maintained substantially the same.

The results show that the sensor output voltage decreases with the increase of carbon within the steel. These results were as expected since the soft magnetic properties of steel are known to decrease with an increase in carbon percentage, the conclusion to be drawn from this is that the sensor device of the present invention is well suited to assess variations in the presence of carbon in the composition of steel.

TEST 4

Detection of Residual Stress in Steel

The sensor device according to the invention was placed at the centre of a tensile steel specimen having the following composition:

| Element | Weight Percentage |
| --- | --- |
| Carbon | 0.025 |
| Manganese | 0.360 |
| Phosphorus | 0.005 |
| Sulphur | 0.011 |
| Copper | 0.011 |
| Aluminium | 0.005 |
| Iron | Balance |

The sensor output voltage was measured when the steel specimen was subjected to stress. It was found that the output voltage increased with tensile stress and reached saturation at higher stress level. This result establishes that the sensor of the present invention is useful in the detection of the residual stress in steel.

The results of the test carried out establish conclusively that the device of the present invention is capable of efficiently determining the presence of ferromagnetic phase in steel and also of ascertaining the change in the magnetic state of the material. Accordingly, the inventive device possesses the advantage of being capable of use for the non-destructive evaluation of in-service ferromagnetic steel components or structures for determining residual stress therein as well as for the sorting and classification of steels according to the compositional variation thereof.

THE MAIN ADVANTAGES OF THE INVENTION

The main advantages of the device of the present invention can be summed up as follows. The device is portable, low cost and easy to use. It can evaluate material properties of steel in a non-destructive way. The device evinces greater sensitivity than other known portable magnetic techniques employed for the non-destructive evaluation of materials. Finally, the device of the present invention is extremely versatile in that it is also useful in the detection of very weak magnetic fields and hence can be employed as a security sensor to detect movement of ferromagnetic objects.

We claim:

1. A portable, easily operable magnetic sensing device for the non-destructive evaluation of steel structures or components which have undergone an extended period of service in order to determine the extent of micro-structural degradation or residual stress within said structures or components which comprises the combination of a probe head adapted to be located proximate the structure or component to be evaluated and signal processing means, characterised in that said probe head comprises a sensing core of nonocrystalline Fe-based material having a first pair of coils wound thereabout such that in normal condition when current flows through said first pair of coils, each half of the sensing core is symmetrically magnetised and said signal processing means comprises a toroidal ferrite core having a second pair of coils wound thereon, one of the terminals of each of said first pair of coils of the sensing core being earthed while the other terminals thereof are each connected respectively to one terminal of each of said second pair of coils on said toroidal core, the other terminals of the second pair of coils being joined together and connected to an excitation source capable of generation of a frequency of 5 kHz, the combination of said first and second pairs of coils constituting a primary, coil, the sensed signal having different harmonics which emanates from said primary coil when the probe head is placed proximate a structure or component being evaluated in order to assess the micro-structural degradation or residual stress thereof being transmitted to the input of a secondary coil mounted on said toroidal core, the output of said secondary coil being connected to a filter means active to suppress only a first harmonic signal and to permit other harmonic signals to pass onward for measurement thereof.

2. A device as claimed in claim 1 wherein the nanocrystallne Fe-based material forming said sensing core is a heat-treated $Fe_{22+k}Nb_{4.5x}Cu_{13.5}B_9$ in which x is a value from 0 to 1, said nanocrystalline ribbon having approximately the following properties:

| | |
|---|---|
| Dimension | 40 mm × 10 mm × 24 μm |
| Permeability | $10^4 \times 10^5$ |
| Coercivity | 10–30 mOe |
| Saturation induction | 8–10 kG |

3. A device as claimed in claim 1 wherein said toroidal core is composed of Mn-Zn ferrite having a permeability of from 3000 to 4000 and a coercivity of from 1 to 3 Oe.

4. A device as claimed in claim 1 wherein said first pair of coils each has the same number of turns which can vary from 1500 to 2000.

5. A device as claimed in claim 1 wherein each of said second pair of coils has the same number of turns which can vary from 25 to 50.

6. A device as claimed in claim 1 wherein said secondary coil has from 50 to 100 turns.

7. A device as claimed in claim 1 wherein said excitation source is a constant current signal generator.

8. A device as claimed in claim 1 wherein said filter means in a notch filter active to suppress the first harmonic, i.e, a signal of 5 kHz and to permit other harmonics, i.e., all signals other than 5 kHz, to pass onward.

9. A device as claimed in claim 1 wherein said means for measuring said second harmonic signal is multimeter.

10. A device as claimed in claim 1 wherein an amplifier is connected to the output of said filter means to which said second harmonic signal is passed for amplification prior to being measured.

11. A device as claimed in claim 10 wherein said amplifier is tuned amplifier which amplifies the second harmonic, i.e. a signal of 10 kHz, to a desired level for the convenient measurement thereof.

* * * * *